(12) United States Patent
Pritchard et al.

(10) Patent No.: US 8,049,020 B2
(45) Date of Patent: Nov. 1, 2011

(54) SUBSTITUTED N-ACYL HOMOSERINE LACTONES

(75) Inventors: David Idris Pritchard, Leicestershire (GB); Siri Ram Chhabra, Leicestershire (GB)

(73) Assignee: The Secretary of State for Defence, Salisbury, Wiltshire (GB)

( * ) Notice: Subject to any disclaimer, the term of this patent is extended or adjusted under 35 U.S.C. 154(b) by 0 days.

(21) Appl. No.: 12/302,258

(22) PCT Filed: May 22, 2007

(86) PCT No.: PCT/GB2007/050284
§ 371 (c)(1),
(2), (4) Date: Nov. 24, 2008

(87) PCT Pub. No.: WO2007/135466
PCT Pub. Date: Nov. 29, 2007

(65) Prior Publication Data
US 2010/0286261 A1      Nov. 11, 2010

(30) Foreign Application Priority Data

May 22, 2006   (GB) .................... 0610042.4

(51) Int. Cl.
*C07D 307/00* (2006.01)
(52) U.S. Cl. .................................... 549/321
(58) Field of Classification Search .......... 549/321
See application file for complete search history.

(56) References Cited

U.S. PATENT DOCUMENTS 6,337,347 B1 *   1/2002   Livinghouse ................. 514/471

FOREIGN PATENT DOCUMENTS

| WO | 92/18614 A | 10/1992 |
| WO | 95/01175 A | 1/1995 |
| WO | 01/74801 A1 | 10/2001 |
| WO | WO 01/74801 | * 11/2001 |

OTHER PUBLICATIONS

Telford et al., The *Pseudomonas aeruginosa* Quorum-Sensing Signal Molecule N-(3-Oxododecanoyl)-L-Homoserine Lactone Has Immunomodulatory Activity. Infection and Immunity (1998) 66:36-42.

* cited by examiner

*Primary Examiner* — Nizal Chandrakumar
(74) *Attorney, Agent, or Firm* — Bozicevic, Field & Francis LLP; Bret E. Field

(57) ABSTRACT

The substituted N-acyl homoserine lactones have the formula (I) wherein R is a saturated or unsaturated straight chain or branched chain aliphatic hydrocarbyl group containing from 5 to 14 carbon atoms; $R^2$ is H or a 1-4C alkyl group; $R^3$ is H or F; and any enantiomer thereof. These compounds exhibit immunosuppressant activity while exhibiting reduced biosensor (autoinducer) activity compared to known N-acyl homoserine lactones.

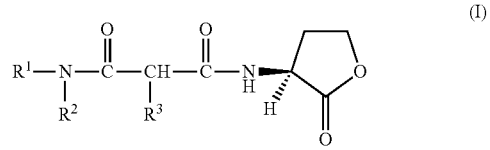

(I)

8 Claims, 2 Drawing Sheets

SUBSTITUTED N-ACYL HOMOSERINE LACTONES

Figure 1:
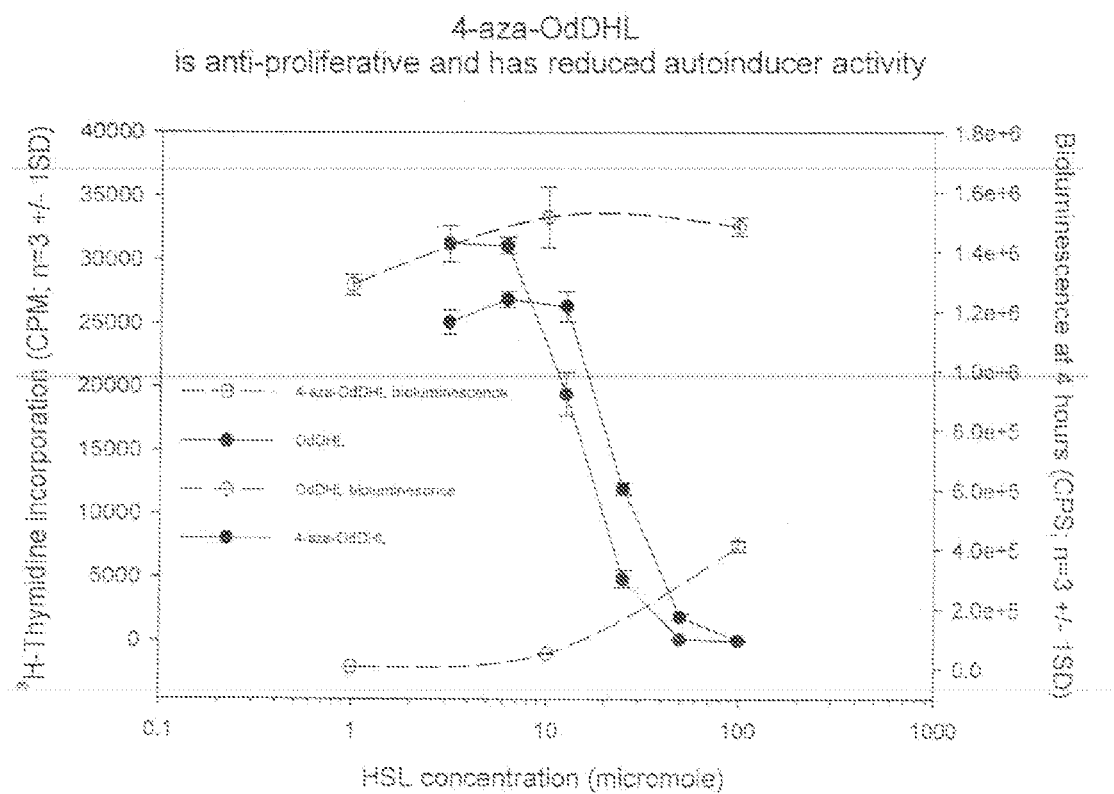

The invention relates to substituted N-acyl homoserine lactones. More particularly, it relates to certain substituted N-acyl homoserine lactones which exhibit immunosuppressant activity while exhibiting reduced biosensor (autoinducer) activity. The invention, further, relates to a pharmaceutical composition containing such a substituted N-acyl homoserine lactone as an active ingredient.

Immunosuppressant compounds induce an inhibition of the immune response system. Compounds which are known to exhibit immunosuppressant activity include the fungal metabolite Cyclosporin A and the macrolide antibiotic (a metabolite from *Streptomyces tsukabaensis*) termed FK506. Both of these agents have been used clinically and experimentally to suppress the immune system in transplantation and in the treatment of a number of diseases.

Autoimmune diseases are disorders where the host discrimination of "self" versus "non-self" breaks down and the individual's immune system (both acquired and innate components) attacks self tissues. These diseases range from common entities, such as rheumatoid arthritis, thyroid autoimmune disease and type 1 diabetes mellitus to less common entities, such as multiple sclerosis and to rarer disorders such as myasthenia gravis. Advances in basic biomedical science and, in particular, in immunology have indicated that the main and fundamental lesion responsible for the induction and persistence of most autoimmune diseases resides within autoreactive proliferating T lymphocytes. In fact, the majority of autoimmune diseases are linked to a loss of T cell homeostasis. The healthy immune system is held in balanced equilibrium, apparently by the contra-suppressive production of cytokines by T helper 1 (Th1) and T helper 2 (Th2) lymphocyte subsets. In autoimmunity, Th1 cytokines predominate; in allergy, Th2 cytokines take their place. A cytokine intimately associated with the development of Th1 biased responses and, consequently, autoimmune disease is TNF-α.

Both Cyclosporin A and FK506 have been used clinically in the treatment of autoimmune diseases with encouraging results.

The currently available immunosuppressant drugs have the disadvantage of a narrow therapeutic index, i.e. toxicity versus clinical benefit. The compounds are known to be nephrotoxic, neurotoxic and potentially diabetogenic and this has limited their use in the fields mentioned above. Problems also exist with the administration of these compounds, their bioavailability and the monitoring of their levels both clinically and in the laboratory.

N-Acyl homoserine lactones are known. WO 92/18614 discloses compounds having the formula

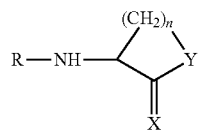

where n is 2 or 3; Y is O, S or NH; X is O, S or NH and R is an optionally substituted $C_1$-$C_{12}$ alkyl or acyl. These compounds were disclosed in that document as autoinducers and as agents for the control of gene expression. A naturally occurring autoinducer is a compound produced by a microorganism during metabolism which then acts to increase the expression of the genes of the microorganism. Compounds in the same series as disclosed in WO 92/18614 are also mentioned in Journal of Bacteriology, volume 175, number 12, June 1993, pages 3856 to 3862 but again there is no teaching that they might have any effect outside microorganisms.

G. Papaccio, Diabetes Res. Clin. Pract. vol. 13, No. 1, 1991, pages 95-102 discloses the use of N-acetylhomocysteine thiolactone as an enhancer of superoxide dismutase in an attempt to increase protection against chemically induced diabetes.

The use of N-acetylhomocysteine thiolactone to modify the IgE molecule is taught by J. Ljaljevic et al in Od. Med. Nauka, vol. 24, 1971, pages 137-143 and Chemical Abstracts, vol. 78, No. 7, February 1973, abstract No. 41213a. However, there is no suggestion in this paper of immunosuppression.

U.S. Pat. No. 5,591,872 discloses the compound N-(3-oxododecanoyl) homoserine lactone as the autoinducer molecule for *Pseudomonas aeruginosa*. In "Infection and Immunity", vol. 66, No. 1, January 1998, the authors report the action of N-(3-oxododecanoyl) homoserine lactone (OdDHL) in inhibiting the concavalin A mitogen stimulated proliferation of murine spleen cells and TNF-α production by LPS-stimulated adherent murine peritoneal macrophages.

In WO 95/01175, a class of compounds related to those compounds previously disclosed in WO 92/18614 was described as exhibiting antiallergic activity and inhibiting histamine release.

A new subclass of immunosuppressant N-acyl homoserine lactones was disclosed in WO 01/74801. These compounds, which may be represented by the formula

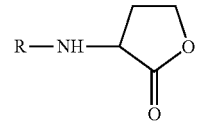

in which R is an acyl group of the formula

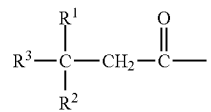

wherein one of $R^1$ and $R^2$ is H and the other is selected from $OR^4$, $SR^4$ and $NHR^4$, wherein $R^4$ is H or 1-6C alkyl, or $R^1$ and $R^2$ together with the carbon atom to which they are joined to form a keto group, and $R^3$ is a straight or branched chain, saturated or unsaturated aliphatic hydrocarbyl group containing from 8 to 11 carbon atoms and is optionally substituted by one or more substituent groups selected from halogen, 1-6C alkoxy, carboxy, 1-6C alkoxycarbonyl, carbamoyl optionally mono- or disubstituted at the N atom by 1-6C alkyl and $NR^5R^6$ wherein each of $R^5$ and $R^6$ is selected from H and 1-6C alkyl or $R^5$ and $R^6$ together with the N atom form a morpholino or piperazino group, or any enantiomer thereof, are reported as being capable of modulating the immune response in the living animal body. In particular, they have an inhibitory effect on lymphocyte proliferation in humans and downregulate TNF-α secretion by monocytes/macrophages and, in consequence, the activation of Th1 lymphocytes in humans. All of these N-acyl homoserine lactones disclosed in the prior art have biosensor activity which is a disadvantage in a compound also possessing anti-proliferative activity. It has been the aim of research workers in this field to find compounds related to OdDHL which have comparable immune modulation properties but which have the advantage that they exhibit reduced biosensor activity. It is to the credit of the inventors that such compounds have now been discovered.

Accordingly, the present invention in a first aspect provides a compound of the formula I (I)

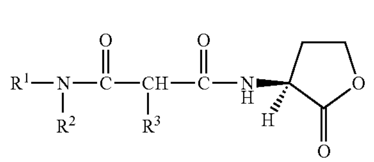

in which $R^1$ is a saturated or unsaturated, straight chain or branched chain aliphatic hydrocarbyl group containing from 5 to 14 carbon atoms; $R^2$ is H, or a 1 to 4C alkyl group; $R^3$ is H or F, and any enantiomer thereof.

The group $R^1$ in the formula I above is a saturated or unsaturated, straight chain or branched chain aliphatic hydrocarbyl group containing from 5 to 14 carbon atoms. For example, $R^1$ may be a straight or branched chain 5 to 14C alkyl group or a straight or branched chain 5 to 14C alkenyl or 5 to 14C alkynyl group. Preferably, $R^1$ is a straight chain alkyl group containing from 5 to 14 carbon atoms. Specific examples of such alkyl groups include pentyl, hexyl, heptyl, octyl, nonyl and decyl groups. According to a particularly preferred embodiment of the invention, the group $R^1$ is n-octyl.

The group $R^2$ in the formula I above is selected from the group comprising H and 1 to 4C alkyl. Examples of 1 to 4C alkyl groups that may be represented by $R^2$ in the formula I above include methyl, ethyl, propyl, isopropyl, n-butyl and isobutyl groups. Preferably $R^2$ in the present invention is either H or methyl.

The group $R^3$ in the formula I above is selected from H and fluoro. It will be apparent that when $R^3$ in the formula I is a fluoro group, an additional chiral centre will be present at the carbon atom to which the fluoro group is attached. The present invention relates to individual enantiomeric forms of the compounds as well as the racemic mixtures.

The preferred compounds according to the present invention have the formula I above in which the group $R^1$ is n-octyl, the group $R^2$ is H or methyl and the group $R^3$ is H or fluoro. Specific examples of compounds that are preferred according to the invention are N-(4-aza-3-oxododecanoyl)-L-homoserine lactone, N-(4-methyl-4-aza-3-oxododecanoyl)-L-homoserine lactone and N-(4-aza-2-fluoro-3-oxododecanoyl)-L-homoserine lactone.

The compounds of the present invention can, in general, be prepared by the reaction of a substituted carboxylic acid having the formula $R^1R^2NC(O)CHR^3C(O)OH$, where $R^1$, $R^2$ and $R^3$ are defined above, with N,N'-carbonyldiimidazole and then reacting the N-acylimidazole intermediate with L-homoserine lactone, typically as the hydrochloride.

The carboxylic acids described above as starting materials in the preparation may, themselves, be obtained by the reaction of the amine $R^1R^2NH$ with an ethyl ester of the optionally-substituted malonic acid to form the ethyl ester of the required substituted carboxylic acid which may then be hydrolysed to the carboxylic acid. For instance, we have found that substituted carboxylic acids of the formula above, wherein $R^3$ is H, can be prepared simply by the reaction of the amine $R^1R^2NH$ with ethyl malonyl chloride and then hydrolysing the resulting ethyl ester to the acid. In the case where the group $R^3$ is a fluoro group, we have found that we can obtain the ethyl ester of the desired substituted carboxylic acid in good yield from the reaction between the amine $R^1R^2NH$ and dimethyl fluoromalonate.

The compounds of the present invention have use as pharmaceutically active ingredients in the treatment of an individual suffering from a disease or disorder which is responsive to the activity of an immunosuppressant. The compounds of the present invention inhibit the proliferation of lymphocytes and the production of TNF-$\alpha$ while, at the same time, exhibiting reduced autoinducer activity compared to OdDHL. Thus, the compounds may be used to modulate the immune system in an individual, for instance in the treatment of autoimmune disease. Specific examples of autoimmune disease that may be treated by the administration of an effective dose of a compound of the invention include psoriasis, multiple sclerosis and rheumatoid arthritis. A dosage to be administered to an individual in need of therapy will, of course, depend on the actual active compound used, the mode of administration and the type of treatment desired as well as on the body mass of the individual. The active compound may be administered on its own or in the form of an appropriate medicinal composition containing, for instance, an appropriate pharmaceutical carrier, excipient or diluent. Other substances can also be used in such medicinal compositions, such as antioxidants and stabilisers, the use of which are well known to persons skilled in the art.

EXAMPLES

Example 1

Synthesis of N-(4-aza-3-oxododecanoyl)-L-homoserine lactone (4-aza-OdDHL)

Step 1. Ethyl 4-aza-3-oxododecanoate

To an ice-cold stirred solution of n-octylamine (101.54 mmol, 13.12 g) in dry dichloromethane (75 ml) was added ethyl malonyl chloride (50.77 mmol, 6.5 ml) dropwise over the period of 15 minutes and further stirred for one hour. The solution was sequentially washed with saturated sodium bicarbonate (3×20 ml), 2 M HCl (3×20 ml) and saturated sodium chloride solution (1×20 ml). Drying over $MgSO_4$ and rotary evaporation of organic solvent gave ethyl 4-aza-3-oxododecanoate as white solid (8.5 g, 69%).

TLC $R_f$ 0.43, Ethyl acetate-hexane (1:1)

$^1H$ NMR (250 MHz, $CDCl_3$) $\delta$ 0.93 (3H, t, J 6.0 Hz, $(CH_3(CH_2)_7)$, 1.07-1.77 (13H, m, $CH_3(CH_2)_5$ and $OCH_2CH_3$), 1.48 (2H, m, $CH_3(CH_2)_5CH_2$), 3.23 (2H, t, J 7.5 Hz, $CH_3(CH_2)_6CH_2$), 3.30 (2H, s, $COCH_2COO$), 4.23 (2H, q, J 7.5 Hz, $OCH_2CH_3$), 7.71 (1H, br s, NH).

Step 2. 4-Aza-3-oxododecanoic acid

To a stirred solution of ethyl 4-aza-3-oxododecanoate (7.5 mmol, 1.81 g) in ethanol (50 ml) was added a solution of NaOH (8.75 mmol, 350 mg) in water (50 ml) and stirring continued at room temperature for 16 hours. This mixture was rotary evaporated to remove ethanol. The residue was redissolved in water and washed with ethyl acetate. It was then acidified with 2 M HCl (pH 1). The product 4-aza-3-oxododecanoic acid was extracted with dichloromethane (4×15 ml). After drying over $MgSO_4$ and rotary evaporation of dichloromethane, 4-aza-3-oxododecanoic acid was obtained as a white solid (1.35 g, 84.3%).

$^1H$ NMR (250 MHz, $CDCl_3$) $\delta$ 0.9 (3H, t, J 6.15 Hz, $CH_3(CH_2)_7$), 1.3 (10H, m, $CH_3(CH_2)_5$), 1.54 (2H, m, $CH_3(CH_2)_5CH_2$—), 3.3 (2H, J 6.4, $CH_3(CH_2)_6CH_2$), 3.37 (2H, s, $COCH_2CO$), 7.19 (1H, s, NH), 10.64 (1H, s, COOH).

Step 3. N-(4-aza-3-oxododecanoyl)-L-homoserine lactone (4-aza-OdDHL)

To a stirred solution of 4-aza-3-oxododecanoic acid (5.74 mmol, 1.23 g) in dry dichloromethane (40 ml) was added sequentially N,N'-carbonyldiimidazole (5.02 mmol, 943 mg), triethylamine (5.74 mmol, 0.8 ml) and L-homoserine lactone hydrochloride (5.74 mmol, 790 mg). The mixture was stirred at room temperature overnight and then solvent rotary evaporated. The residue was redissolved in ethyl acetate (40 ml) and the solution washed with saturated sodium bicarbonate (2×25 ml), 2 M HCl (3×25 ml) and brine (1×25 ml). After drying over $MgSO_4$ and removal of solvent in vacuum, the isolated product 4-aza-OdDHL was purified by PLC using Hexane-Ethyl acetate (1:4) solvent system (676 mg, 39.5%)

TLC $R_f$ 0.23, Ethyl acetate-hexane (4:1)
IR (KBr) 3293 (NH), 1771 (ring C=O), 1685 (3-amide C=O), 1645 (1-amide C=O) $cm^{-1}$
$^1$H NMR (250 MHz, $CDCl_3$) δ 0.9 (3H, t, J 6.5 Hz, $CH_3$ $(CH_2)_7$), 1.27 (10H, m, $CH_3(CH_2)_5$), 1.5 (2H, br, $CH_3(CH_2)_5$ $CH_2$) 2.34 (1H, dd, J 9.9 and 1.5 Hz, ring, 4α-H), 2.66 (1H, ddd, J 2.0, 3.8 and 6.8 Hz, ring, 4β-H), 3.22 (2H, t, J 6.6 Hz, $CH_3(CH_2)_6CH_2$), 3.28 (2H, s, $COCH_2CO$), 4.23 (1H, ddd, J 3.0, 4.4 and 6.3 Hz, ring, 3H), 4.49 (1H, dd, J 7.65 and 1.3 Hz, ring, 5α-H), 4.6 (1H, ddd, J 2.3, 4.9 and 8.7 Hz, ring, 5β-H), 7.14 (1H, br t, 4-NH), 8.2 (1H, d, J 6.8 Hz, NH-HSL).
ES-MS m/z 299.13 (M+H, $C_{15}H_{26}N_2O_4$ requires m/z 298), 321.11 (M+Na).

Example 2

Synthesis of N-(4-aza-4-methyl-3-oxododecanoyl)-L-homoserine lactone (4-aza-4-Me-OdDHL)
Step 1. Ethyl 4-aza-4-methyl-3-oxododecanoate The procedure described above in Example 1, step 1, was repeated except that N-methyl-n-octylamine was used instead of n-octylamine. The title product was obtained as a semisolid that was recrystallised from diethyl ether (97%).

TLC $R_f$ 0.5, Ethyl acetate-hexane (1:1)
$^1$H NMR (250 MHz, $CDCl_3$) δ 0.87 (3H, t, J 6.7 Hz, $(CH_3(CH_2)_7)$, 1.26-1.32 (13H, m, $CH_3(CH_2)_5$ and $OCH_2CH_3$), 1.55 (2H, s (broad), $CH_3(CH_2)_5CH_2$), 2.94, 2.98 (3H, 2×s, $NCH_3$), 3.24 (1H, dd, J 1.9 and 7.6 Hz, $CH_3(CH_2)_6$ $CH(H)$), 3.39 (1H, ddd, J 1.9, 5.6 and 7.6 Hz, $CH_3(CH_2)_6CH$ (H)), 3.44 (2H, s, $COCH_2COO$), 4.2 (2H, two q (overlap), $OCH_2CH_3$).
Step 2. 4-Aza-4-methyl-3-oxododecanoic acid Ethyl 4-aza-4-methyl-3-oxododecanoate (4.85 mmol, 1.246 g) was saponified with a solution of NaOH (5.7 mmol, 226 mg) according to the procedure described above for ethyl 4-aza-3-oxododecanoate in Example 1, Step 2. The product 4-aza-4-methyl-3-oxododecanoic acid was obtained as a white solid (1.03 g, 93%).

$^1$H NMR (250 MHz, $CDCl_3$) δ 0.89 (3H, t, J 6.0 Hz, $(CH_3(CH_2)_7)$, 1.3 (10H, m, $CH_3(CH_2)_5$), 1.58 (2H, br s, $CH_3$ $(CH_2)_5CH_2$), 3.03 (3H, s, $NCH_3$), 3.24 (2H, J 7.6 Hz, $CH_3$ $(CH_2)_6CH_2$), 3.42 (2H, s, $COCH_2COO$), 10.15 (1H, s, COOH).
Step 3. N-(4-aza-4-methyl-3-oxododecanoyl)-L-homoserine lactone (4-aza-4-Me-OdDHL)

4-Aza-4-methyl-3-oxododecanoic acid (3.9 mmol, 896 mg) was coupled with L-homoserine lactone hydrochloride (4.0 mmol, 550 mg) according to the procedure described in Example 1, Step 3. The title product, 4-aza-4-methyl-OdDHL was purified by PLC in Hexane-Ethyl acetate (1:4), (237 mg, 19.5%).

TLC $R_f$ 0.19, Ethyl acetate-hexane (4:1)
IR (KBr) 3299 (NH), 1776 (ring C=O), 1683 (3-amide C=O), 1654 (1-amide C=O) $cm^{-1}$
$^1$H NMR (250 MHz, $CDCl_3$) 0.88 (3H, t, J 5.6 Hz, $(CH_3$ $(CH_2)_7)$, 1.27 (10H, m, $CH_3(CH_2)_5$), 1.53 (2H, br s, $CH_3$ $(CH_2)_5CH_2$), 2.29 (1H, dd, J 10.1 and 1.47 Hz, ring, 4α-H), 2.66 (1H, dd, J 2.0 and 5.6 Hz, ring, 4β-H), 3.0 (3H, 2×s, $NCH_3$), 3.3 (2H, t, J 7.72 Hz, $CH_3(CH_2)_6CH_2$), 3.38 (2H s, $COCH_2CO$), 4.28 (1H, dddd, 1.49, 3.19, 4.05 and 6.1 Hz, ring, 3H), 4.48 (1H, t, J 9.1 Hz, ring, 5α-H), 4.6 (1H, dddd, J 1.5, 2.6, 4.5 and 7.2 Hz, ring, 5β-H), 8.84 (1H, d, J 7.4 Hz, NH-HSL).
ES-MS m/z 313.14 (M+H, $C_{16}H_{28}N_2O_4$ requires m/z 312), 335.12 (M+Na).

Example 3

4-Aza-2-fluoro-3-oxododecanoyl-L-homoserine lactone (4-aza-2-F-OdDHL)

Step 1. Methyl 4-aza-2-fluoro-3-oxododecanoate

To a stirred solution of dimethyl fluoromalonate (1 mmol, 150.11 mg) in anhydrous methanol (10 ml) was added a solution of n-octylamine (1 mmol, 166 μl) in methanol (5 ml) drop wise over the period of one hour at room temperature. It was then further stirred at room temperature for two hours. The solution was rotary evaporated and the residue redissolved in ethyl acetate. The ethyl acetate solution was sequentially washed with 2 M HCl (2×10 ml) and saturated sodium chloride (1×15 ml) solution. Drying over $MgSO_4$ and rotary evaporation of organic solvent gave white solid that was a mixture of bisamide and ethyl 4-aza-2-fluoro-3-oxododecanoate. Desired product was purified as a white solid by PLC in 40-60 petroleum ether-diethyl ether (3:2), (117 mg, 47%).

TLC $R_f$ 0.23, petroleum ether-diethyl ether (3:2)
$^1$H NMR (400 MHz, $CDCl_3$) δ 0.88 (3H, t, J 6.4 Hz, $(CH_3(CH_2)_7)$, 1.29 (10H, m, $CH_3(CH_2)_5$), 1.54 (2H, br s, $CH_3(CH_2)_5CH_2$), 3.32 (2H, m, J 6.6 Hz, $CH_3(CH_2)_6CH_2$), 3.9 (3H, s, $OCH_3$), 5.28 (1H, d, J 49.2, C(H)F), 6.42 (1H, s, NH).
Step 2. 4-Aza-2-fluoro-3-oxododecanoic acid To a stirred solution of methyl 4-aza-2-fluoro-3-oxododecanoate (0.28 mmol, 70 mg) in methanol (15 ml) was added a solution of NaOH (0.28 mmol, 11.2 mg) in water (5 ml) and further stirred at room temperature for two hours. This mixture was rotary evaporated to remove methanol. The residue was redissolved in water (25 ml) and aqueous solution was washed with ethyl acetate. It was then acidified with 2 M HCl (pH 1). The product 4-aza-2-fluoro-3-oxododecanoic acid was extracted in ethyl acetate (3×15 ml). After drying over $MgSO_4$ and rotary evaporation of ethyl acetate, 4-aza-2-fluoro-3-oxododecanoic acid was obtained as a white solid (64 mg, 99%).

$^1$H NMR (400 MHz, $CDCl_3$) δ 0.9 (3H, t, J 6.6 Hz, $(CH_3$ $(CH_2)_7)$, 1.31 (10H, m, $CH_3(CH_2)_5$), 1.60 (2H, m, $CH_3$ $(CH_2)_5 CH_2$), 3.4 (2H, J 6.8 Hz, $CH_3(CH_2)_6CH_2$), 5.3 (1H, d, J 47.2 Hz, C(H)F), 6.7 (1H, s, NH), 7.3 (1H, br s, COOH)
Step 3. 4-Aza-2-fluoro-3-oxododecanoyl-L-homoserine lactone (4-aza-2-F-OdDHL)

To a stirred solution of 4-aza-2-fluoro-3-oxododecanoic acid (0.28 mmol, 64 mg) in dry dichloromethane (20 ml) was added sequentially 1,1'-carbonyldiimidazole (0.3 mmol, 49 mg), triethylamine (0.3 mmol, 42 μl) and L-homoserine lactone hydrochloride (0.3 mmol, 42 mg). This mixture was stirred at room temperature overnight and then solvent rotary evaporated. The residue was redissolved in ethyl acetate (30 ml). The ethyl acetate solution was washed with saturated sodium bicarbonate (2×20 ml), 1 M KHSO$_4$ (2×20 ml) and brine (1×20 ml). It was dried over MgSO$_4$ and solvent rotary evaporated. The product 4-aza-4-methyl-OdDHL was purified by PLC in ethyl acetate (8.2 mg, 10.4%).

TLC R$_f$ 0.32, Ethyl acetate

IR (KBr) 3298 (NH), 1772 (ring C=O), 1683 (3-amide C=O), 1653 (1-amide C=O) cm$^{-1}$ $^1$H NMR (400 MHz, CDCl$_3$) 0.89 (3H, t, J 6.9 Hz, (CH$_3$ (CH$_2$)$_7$), 1.3 (10H, m, CH$_3$(CH$_2$)$_5$), 1.56 (2H, m, CH$_3$(CH$_2$)$_5$ CH$_2$), 2.27 (1H, dd, J 8.97 and 2.3 Hz, ring, 4α-H), 2.80 (1H, ddd, J 1.4, 2.54 and 5.34 Hz, ring, 4β-H), 3.33 (2H, m, CH$_3$(CH$_2$)$_6$CH$_2$), 4.28 (1H, dd, J 1.4 and 4.5 Hz, ring, 3H), 4.53 (1H, m, ring, 5α-H), 4.64 (1H, ddd, J 2.64, 2.94 and 4.14 Hz, ring, 5β-H), 5.3 (1H, dd, J 10.2 and 38.0 Hz, CF(H)), 6.63 (1H, s, 4-NH), 7.5 (1H, dd, J 13.3, 6.4 Hz, NH-HSL).

ES-MS m/z 317.12 (M+H, C$_{15}$H$_{25}$FN$_2$O$_4$ requires m/z 316), 339.09 (M+Na).

Immunomodulatory Activity of Homoserine Lactone Compounds

Materials and Methods

I. ConA Mitogen-Stimulated Proliferation of Murine Splenocytes

The concanavalin A (ConA) cell proliferation assay was used to assess the effect of test homoserine lactone (HSL) compounds on T-cell activation and proliferation. Proliferation was assessed by the incorporation of [$^3$H]-thymidine into DNA. Eight-week-old female BALB/c mice were obtained from Harlan (Bicester, Oxon, UK) and given food and water ad libitum. Splenocyte suspensions were prepared by removing the spleens and placing them into RPMI 1640 medium. The spleens were forced through 70-µm-pore-size wire gauzes using the plunger from a 5-ml syringe to produce a single cell suspension. The cells were pelleted by centrifugation, and erythrocytes were lysed with 0.017 M Tris, 0.144 M ammonium chloride buffer, pH 7.2. Leucocytes were washed twice with RPMI 1640 medium with 2% (vol/vol) foetal calf serum (FCS) and resuspended in complete cell culture medium (CTCM) consisting of RPMI 1640 medium with 5% FCS, 2 mM L-glutamine, and 5×10$^{-5}$ M 2-mercaptoethanol. HSL compounds were tested at doubling down dilutions ranging from 1 mM to 0.1 µM in a final volume of 200 µl of CTCM, containing ConA (Sigma, Poole, UK) at 1 µg/ml and 100,000 spleen cells. Following incubation for 48 h at 37° C. in 5% CO$_2$-air, 0.25 µCi[$^3$H]-thymidine (Amersham) in 10 µl volume made up in RPMI 1640 medium was added and the cells were incubated for a further 24 h. Cells were harvested onto fibreglass filters with a Packard filtermate harvester. After the addition of 25 µl of MicroScint-O (Packard) to each well, the filters were counted with the Packard TopCount scintillation counter.

Mitogen (Concanavalin A) induced murine splenocyte proliferation was indicated by the incorporation of tritated thymidine into the DNA in the mouse spleen cells as shown by counts per minute using the scintillation counter. The inhibitory effect of an HSL compound being tested on cell proliferation was indicated by a reduction in counts per minute.

Figure 2:
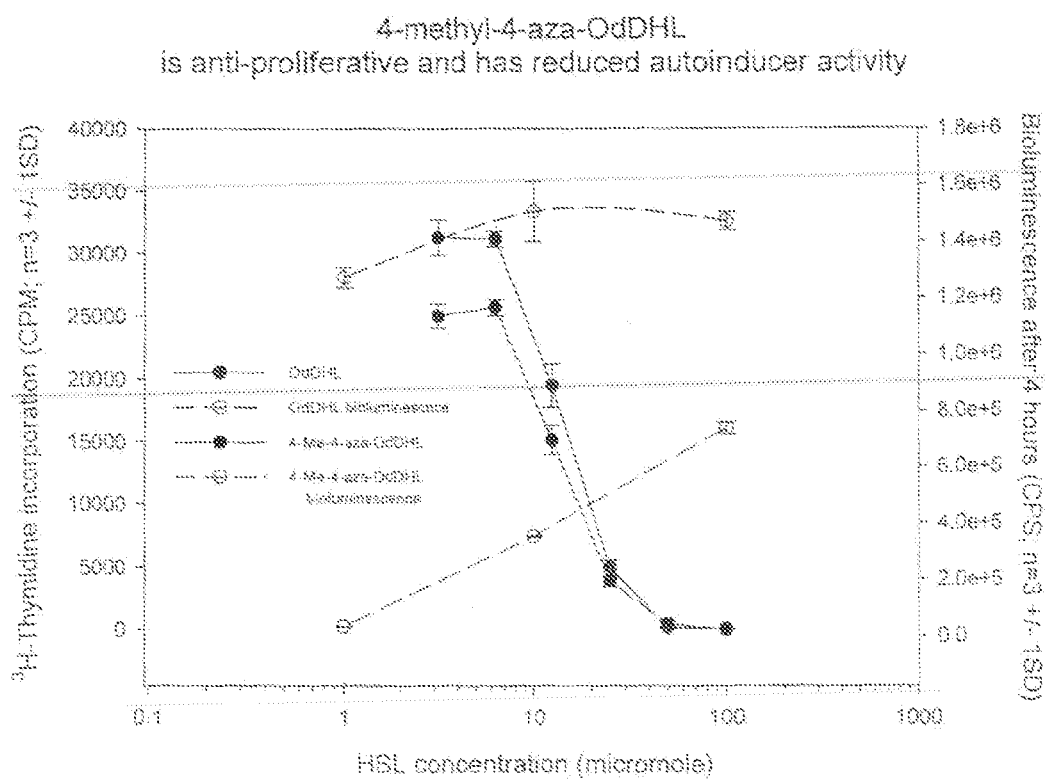

FIG. 1 shows the plots of counts per minute (CPM) against the concentrations (micromolar) of the prior art compound OdDHL and the compound N-(4-aza-3-oxododecanoyl)-L-homoserine lactone (4-aza-OdDHL). As can be seen from this Figure, 4-aza-OdDHL, like OdDHL, inhibits splenocyte proliferation. FIG. 2 shows plots similar to those in FIG. 1 except, here, a comparison is made of the plot obtained for OdDHL with that obtained for the compound N-(4-methyl-4-aza-3-oxododecanoyl)-L-homoserine lactone (4-methyl-4-aza-OdDHL). As shown in FIG. 2, the compound 4-methyl-4-aza-OdDHL inhibits splenoctye proliferation. FIGS. 1 and 2 also show the plots of autoinducer activity of the HSL compounds against HSL concentration (micromolar).

The IC$_{50}$ value, i.e. the dose of compound (micromolar) required to inhibit 50% of a proliferating population of murine splenocytes, was determined for 4-aza-OdDHL, 4-methyl-4-aza-OdDHL and for the compound N-(2-fluoro-4-aza-3-oxododecanoyl)-L-homoserine lactone (2-fluoro-4-aza-OdDHL).

Also determined for each of these compounds was the autoinducer activity as a measure of the ability of the compound to induce light production in a specifically designed bacterial bioreporter system. Autoinducer (A.I.) activity was measured by the ability of the test N-acyl homoserine lactone compound (AHL) to induce bioluminescence in *E. coli* containing a lux-based bioluminescence reporter plasmid. For detection of a long chain AHL, such as OdDHL, *E. coli* JM109 harbouring the reporter plasmid pSB1075 was used. This reporter contains the *P. aeruginosa* IasR gene and IasI promoter fused to IuxCDABE from *P. luminescens* and preferentially responds to AHLs with acyl chains of 10-14 carbons in length.

Bioassays were performed in 96 well microliter plates. Briefly, 10 µl of the compound being assessed was placed into a microliter well plate and serially diluted using LB broth to produce a concentration range from 100 µM to 100 fM. Similar dilutions were performed on a synthetic OdDHL and used as a positive control. One hundred microliters of an overnight biosensor strain was added to each well and light emission was measured following 4 hours incubation at 37° C. Light production was assessed as counts per second on Perkin Elmer TopCount apparatus calibrated to measure bioluminescence. Values are expressed as a percentage of the bioluminescence measured after exposure of the bioreporter to OdDHL for four hours at 37° C. Logarithmic regression analysis of the range of synthetic OdDHL dilutions typically returned coefficient of determination values above 0.96.

The IC$_{50}$ (µM) and A.I. activity (10 µM) values obtained for the test compounds and for OdDHL are shown in the following Table.

| Name | Structure | IC$_{50}$* (µM) | AI activity** (10 µM) |
|---|---|---|---|
| 4-aza-OdDHL | | 17.1 | 2.8% |
| 2-fluoro-4-aza-OdDHL | | 21.8 | 19.9% |
| 4-methyl-4-aza-OdDHL | | 14.6 | 23.2% |
| OdDHL | | 12.7 | 100.0% |

*IC$_{50}$ = dose of compound required to inhibit 50% of a proliferating population of murine splenocytes. Measured using [$^3$H]-thymidine incorporation as a marker of proliferation and determined by nonlinear regressions analysis. All coefficient of determination values were in excess of 0.98.

**Autoinducer activity is a measure of the ability of the compound to induce light production in a specifically designed bacterial bioreporter system.

Values are expressed as a percentage of the bioluminescence measured after exposure of the bacteria to OdDHL for 4 hours at 37° C.

The invention claimed is:

1. A compound of the formula I,

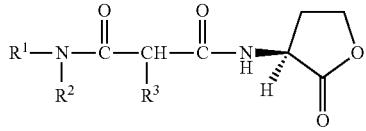

wherein $R^1$ is a saturated or unsaturated straight chain or branched chain aliphatic hydrocarbyl group containing from 5 to 14 carbon atoms; $R^2$ is H or a 1-4C alkyl group; $R^3$ is H or F; and any enantiomer thereof.

2. A compound according to claim 1, wherein $R^1$ is a straight chain alkyl group containing from 5 to 14 carbon atoms.

3. A compound according to claim 2, wherein $R^1$ is a n-octyl group.

4. A compound according to any one of claims 1 to 3, wherein the group $R^2$ is selected from H or a methyl group.

5. A compound according to claim 1 which is N-(4-aza-3-oxododecanoyl)-L-homoserine lactone.

6. A compound according to claim 1 which is N-(4-methyl-4-aza-3-oxododecanoyl)-L-homoserine lactone.

7. A compound according to claim 1 which is N-(4-aza-2-fluoro-3-oxododecanoyl)-L-homoserine lactone.

8. A pharmaceutical composition comprising, as active component, a compound according to any one of claims 1 to 7 and one or more pharmaceutically-acceptable carrier, excipient or diluent.

* * * * *